Figure 1:
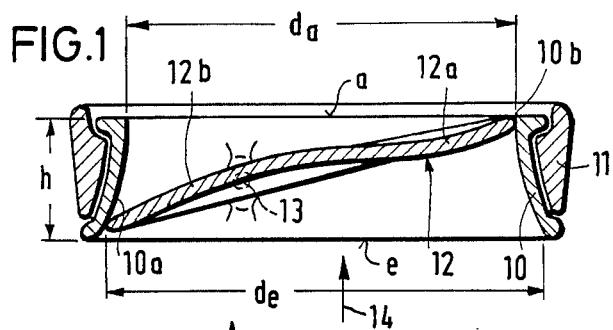

United States Patent [19]
Knoch et al.

[11] Patent Number: 4,799,930
[45] Date of Patent: Jan. 24, 1989

[54] CARDIAC VALVE PROSTHESIS

[75] Inventors: Martin Knoch, Aachen; Helmut Reul, Düren; Günter Rau, Aachen, all of Fed. Rep. of Germany

[73] Assignee: B. Braun Melsungen AG, Melsungen, Fed. Rep. of Germany

[21] Appl. No.: 145,882

[22] Filed: Jan. 20, 1988

[30] Foreign Application Priority Data

Jan. 22, 1987 [DE] Fed. Rep. of Germany ....... 3701755

[51] Int. Cl.$^4$ ................................................ A61F 2/24
[52] U.S. Cl. ................................................ 623/2
[58] Field of Search ................................................ 623/2

[56] References Cited
U.S. PATENT DOCUMENTS 3,926,215 12/1975 MacLead .............................. 623/2
4,328,592 5/1982 Klawitter .............................. 623/2

Primary Examiner—Richard J. Apley
Assistant Examiner—James Prizant
Attorney, Agent, or Firm—Spensley Horn Jubas & Lubitz

[57] ABSTRACT

A cardiac valve prosthesis in which the inner area of the valve ring has an internal cross section continuously decreasing in flow direction. The valve ring is shaped like a nozzle, and flow disruption occurs only at the nozzle end, allowing a concentric flow discharge. Vortex formation at the jet boundary and inside the flow is inhibited. As a result, flow resistance is reduced and blood damage is minimized. A flushing channel traverses the joint cavity in order to avoid deposits of blood particles in the valvular joint.

8 Claims, 2 Drawing Sheets

CARDIAC VALVE PROSTHESIS

The invention relates to a cardiac valve prosthesis.

Natural cardiac valves are of the tricuspid or biscupid type which, technically speaking, function as nonreturn valves allowing blood to flow unidirectionally, while the counterdirection is blocked. If natural cardiac valves are replaced by mechanical prostheses of the pendulum type or tilting disk type, monocuspid or bicuspid valves are inserted wherein valvular closing bodies in a valve ring fixed by sewing at the respective heart opening are movable by blood pressure or blood flow. However, from a long-term use of such cardiac valve prosthesis, serious problems which may result for a patient may entail his lifelong taking of anticoagulants or an interchange of the prosthesis. There is, for instance, the risk of thrombus formation at the valve ring or at the holding means of the closing body so that the mobility of the latter and the tightness of the cardiac valve prosthesis may be impaired. Further, body tissue may grow into the flow area of the blood.

In the design of known cardiac valve prostheses, particular attention had been paid to the inner valve ring surface such that it was adapted to form a sealing abutment surface for the closing body. Thus, the inner surface of the valve ring has been conformed to the peripheral surface of the closing body so that, in closing condition of the closing body, a clamping-free and well sealing seat is ensured. To this effect, the inner face of the valve ring is frequently provided with abutment or sealing edges. British Pat. No. 1,447,871 discloses a valve ring having an inner face which, in axial direction, smoothly changes its nozzle shape. The inner surface is flared towards the outlet opening and is so formed that the closing body profile which is of of the aircraft wing type may sealing adjoin said face. The contour of the inner face is shaped like a hyperboloid, however, the inner surface is not rotationally symmetric. This kind of cardiac valve prosthesis comprising a valve ring passage flared in flow direction is exposed to the risk that already in the central area of the inner surface, the flow may be disrupted therefrom; as a result, blood flow is induced to early vortex formation. The flow is not conducted over a long length as in case of a natural cardiac valve. By the annular vortex formation caused by the valve ring, shearing stresses are generated in the blood which thus may be damaged accordingly. Moreover, also in opened condition, the cardiac valve prosthesis offers a relatively high flow resistance which is caused by a strong contraction of the jet flow discharged from the ring.

It is an object of the invention to provide a cardiac valve prostheses wherein flow resistance is low and the risk of blood damage and thrombus formation is reduced.

In case of the cardiac valve prosthesis of the invention, the cross sectional area of the valve ring is continuously reduced in flow direction thus bringing about, in flow direction, an increasing concentration of the flow lines which, near the wall, follow the contour of the inner ring surface. A uniform and continuous flow through the valve ring is ensured accordingly. The flow discharge is parallel to the longitudinal axis of the valve ring, said flow continuing behind the valve ring over a considerable length without substantial boundary vortices. Hence, shearing forces in the blood flow are reduced to a minimum such that blood is not damaged accordingly. Further, by the increasing velocity in flow direction within the wall boundary layer, the tendency of thrombus formation at the valve ring is reduced.

The articulation points by which the closing body is connected to the valve ring are critical areas at which a thrombus may form preferably. Due to the features specified in the claims, the blood constantly flows around the joint projections thus preventing blood particles from adhering thereto. The support of the joint projections at the joint cavities is not areal, but it is formed by punctiform or linear contact areas exposed to blood flow. Blood flows through the joints at a relatively high speed thus reducing the risk of deposits.

The invention is not only applicable to cardiac valve prostheses having a single closing body, but it is well suited also to bicuspid prostheses or prostheses which, like natural cardiac valves, are provided with three closing bodies.

Preferably, the inner surface of the valve ring—except for the joint points—is designed as a rotationally symmetric surface thus producing an axially symmetric flow.

The cardiac valve prosthesis may be used not only for aortic and pulmonary valves, through which blood is pumped from the heart into the arterial system, but also for mitral and tricuspid valves through which blood is returned from the atria into the heart.

Figure 3:
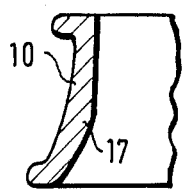
Figure 2:
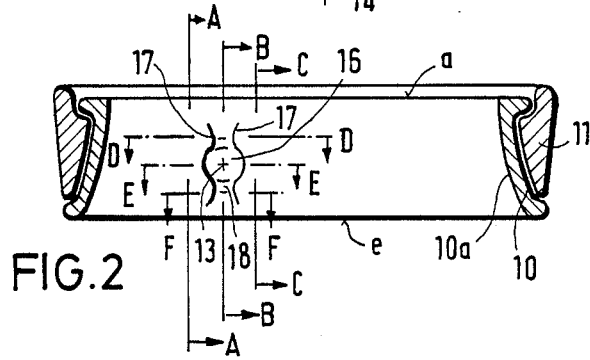
Figure 4:
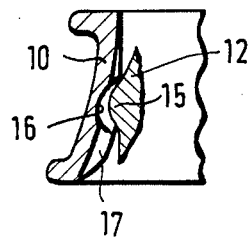
Figure 6:
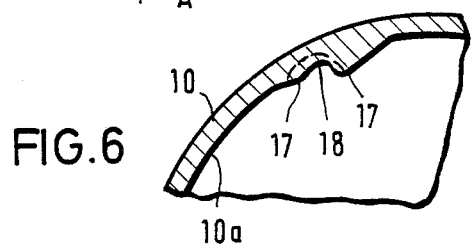
Figure 5:
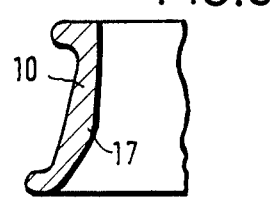
Figure 7:
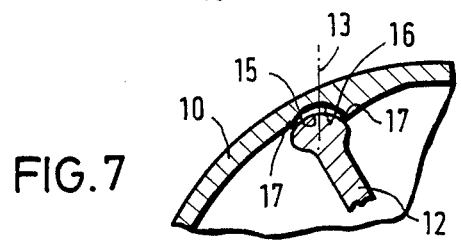
Figure 8:
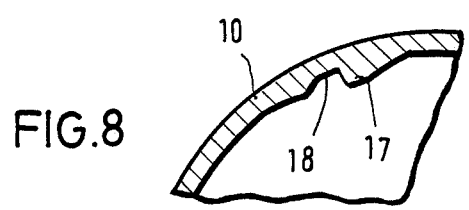
Figure 10:
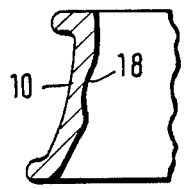
Figure 9:
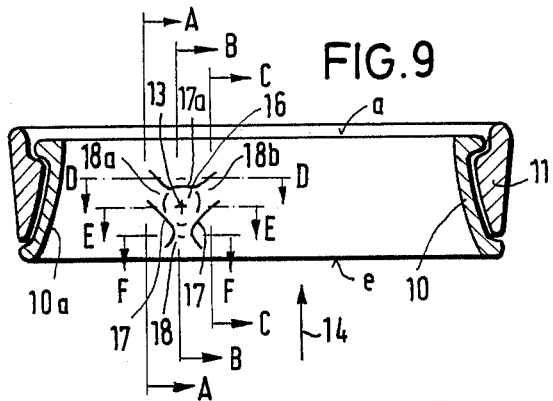
Figure 11:
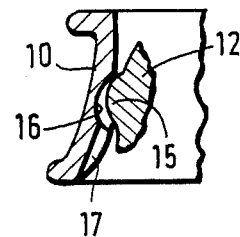
Figure 12:
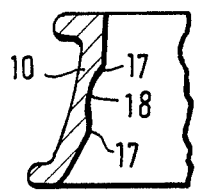
Figure 13:
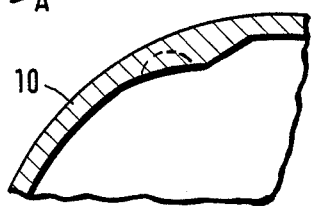
Figure 14:
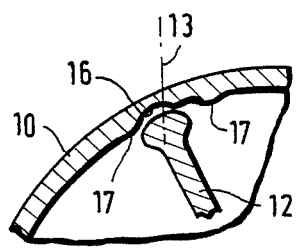
Figure 15:
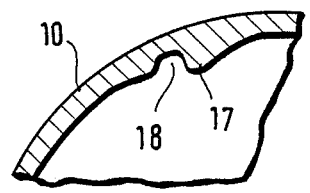

Embodiments of the invention will be explained hereunder in more detail with reference to the drawings in which FIG. 1 is a longitudinal section of a cardiac valve prosthesis, FIG. 2 is the same view as FIG. 1, but without the closing body, to better show a bearing point and the flushing channel, FIG. 3 is a section along line A—A of FIG. 2, FIG. 4 is a section along line B—B of FIG. 2, FIG. 5 is a section along line C—C of FIG. 2, FIG. 6 is a section along line D—D of FIG. 2, FIG. 7 is a section along line E—E of FIG. 2, FIG. 8 is a section along line F—F of FIG. 2, FIG. 9 is a view similar to FIG. 2 showing a valve ring with modified bearing and Y-shaped flushing channel and FIGS. 10 to 15 are cross sectional views similar to FIGS. 3 to 8, however, in connection with the embodiment of FIG. 9.

The cardiac valve prosthesis of FIG. 1 comprises a valve ring 10 of a substantially circular cross section, and having at its periphery a sewing ring 11 for fixing the cardiac valve to the body tissue. In valve ring 10, a valvular closing body 12 is supported to be pivotal about axis 13 extending transversely to the ring axis. Axis 13 is spaced from the ring axis so that the closing body 12 forms two wing sections 12a and 12b of different sizes and separated by the valve axis 13. By this means, the closing body 12 may be opened by the blood pressure effective in direction of arrow 14, while it is caused to take the closing position by a counteracting blood pressure.

The diameter of the inner surface 10a of the valve ring 10 smoothly chages without any kink line from the inlet end to the outlet end, the inner surface 10a being bulged or arched towards the longitudinal axis of the valve ring. The inlet cross section e and the outlet cross section a are circular. Except for the bearing points, the inner surface 10a is rotationally symmetric to the ring axis. At the outlet-sided end of the valve ring 10, the inner surface 10a ends in a sharp edge 10b. Said inner surface 10a forms a nozzle channel having a cross section which constantly decreases in flow direction and which (with closing body 12 in opening condition) is responsible for a smooth and nearly vortex-free jet flow.

In the preferred embodiment of the present invention, if $A_e$ is the surface area of the inlet cross section e while $A_a$ is the surface area of the outlet cross section a, the surface ratio $A_a:A_e$ is 0.64 to 0.90.

The corresponding diameter ratio $d_a:d_e$ between outlet diameter $d_a$ and inlet diameter $d_e$ is 0.80 to 0.95. The ratio of height h to outlet diameter $d_a$ is preferably 0.2 to 0.3.

The vault of the inner surface 10a preferably forms a circular arc. At the outlet end, the inner face 10a extends in parallel to the ring axis, i.e. the tangent to the inner surface 10a at the outlet is parallel to the ring axis.

Due to the above disclosed form of the inner face 10a, blood flowing in direction of arrow 14 is contracted in valve ring 10, while, downstream of the latter, the flow lines extend nearly in parallel, thus generating a jet flow free of vortices as far as well behind the valve ring. An early formation of boundary vortices is avoided by the sharp edge 10b.

One of the two joints provided along the swivel axis 13 of the closing body will be disclosed hereinafter with reference to FIGS. 2 to 8.

At the peripheral surface of closing body 12, two joint projections 15 extending in opposite directions are designed as spherical cups protruding each into a joint cavity 16 formed in the interior of valve ring 10. The joint cavity 16 is limited laterally by two elevations 17 rising from the inner face 10a towards the valve ring inside, said elevations 17 forming first (seen in flow direction) an inlet area in which they converge, i.e. their mutual distance is reduced, secondly a joint area in which their distance first increases to then decrease again and, finally, an outlet area in which their mutual distance is increased again (FIG. 2). Between the elevations 17, there is a flushing channel 18 substantially extending in flow direction. The diameter of the joint projection 15 is so dimensioned that the latter cannot fully disappear in the joint cavity 16 and will find a support at the elevations 17 at both sides of the joint cavity, such as illustrated in FIGS. 4 and 7. Hence, between the arc of the joint connection 15 and the joint cavity, a space is left for blood to flow therethrough. Each joint projection 15 only laterally adjoins two points at the elevations 17, while it is flooded with blood flowing through the flushing channel 18. The velocity of the blood here is relatively high to inhibit a possible thrombus formation. Due to the convergent inlet portion of the flushing channel 18, the blood velocity in the joint cavity 16 is increased, while, by the diverging outlet area, blood from the flushing channel 18 is perfectly integrated again into the main blood stream.

In case of the embodiment of FIGS. 9 to 15, the flushing channel 18 limited laterally by elevations 17, comprises an inlet portion of the same design as that shown in the first embodiment. Therebehind, the flushing channel 18 assumes an Y-shape to form two branches 18a and 18b. The joint cavity 16 is enclosed by three elevations 17, 17a which form a seat for the joint projection 15 and which are so closely adjacent to each other that the joint projection 15 may not penetrate as far as to the bottom of the joint cavity 16. By this means, the joint projection 15, while being retained in the joint against displacements, may easily rotate at low friction without an areal contact to the joint cavity. On the other hand, blood flows around and behind the closing body 12 in any optional position thereof.

What is claimed is:

1. Cardiac valve prosthesis for controlling fluid flow comprising:
   a valve ring having an inner face and in which at least one valvular closing body is pivotally supported,
   the inner face of the valve ring defining a nozzle channel having a cross section which smoothly, continuously and curvilinearly decreases in a direction perpendicular to the valve ring axis, whereby the inner face of the valve ring is continuously and increasingly constricted over its entire length in the direction of fluid flow.

2. Cardiac valve prosthesis as defined in claim 1, wherein said valve ring further includes an inlet-side and an outlet-side, and, at the outlet-side of the valve ring, the inner face of the valve ring has a sharp edge, said sharp edge thereby enabling a flow discharge in parallel to the valve ring axis.

3. Cardiac valve prosthesis as defined in claim 1, wherein the valvular closing body further includes at least two joint projections, wherein the inner face of the valve ring has a joint cavity defined therein, the valvular closing body being supported in the joint cavity of the valve ring by means of the two joint projections, and wherein the inner face of the valve ring has defined therein at least one flushing channel which forms a support for the joint projections.

4. Cardiac valve prosthesis as defined in claim 3, wherein the inner face of the valve ring further includes at least two elevations adjacent the flushing channel, the elevations being mutually spaced to support the joint projection and to define a free space between the joint projection and the flushing channel.

5. Cardiac valve prosthesis as defined in claim 3, wherein the flushing channel forms a Y-branch.

6. A cardiac valve prosthesis for regulating fluid flow comprising:
   a valve ring having a fluid inlet side, a fluid outlet side and an internal surface having a substantially circular cross section, the internal surface cross section decreasing smoothly, continuously and curvilinearly in size from the fluid inlet side to the fluid outlet side,
   at least one valvular closing body pivotally supported in the valve ring,
   whereby a smooth and substantially vortex free fluid flow is permitted.

7. A cardiac valve prosthesis as defiend in claim 6 wherein the valve ring further includes a substantially sharp edge at the fluid outlet side, whereby the formation of boundary vortices is reduced.

8. A cardiac valve prosthesis as defined in claim 6 further comprisng:
   a joint projection extending from the valvular body,
   retainer means disposed in the internal surface of the valve ring for retaining the joint projection,
   the joint projection and the retainer means being mutually configured to define therebetween at least one flushing channel extending in the direction of fluid flow.

* * * * *